(12) United States Patent
Benn

(10) Patent No.: US 10,016,186 B2
(45) Date of Patent: Jul. 10, 2018

(54) SURGICAL INSTRUMENT AND SYSTEM

(71) Applicant: GYRUS MEDICAL LIMITED, Cardiff (GB)

(72) Inventor: Christopher Charles Benn, Bristol (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1049 days.

(21) Appl. No.: 13/679,327

(22) Filed: Nov. 16, 2012

(65) Prior Publication Data

US 2013/0138096 A1 May 30, 2013
US 2018/0078245 A9 Mar. 22, 2018

(30) Foreign Application Priority Data

Nov. 16, 2011 (GB) .................................. 1119769.6

(51) Int. Cl.
*A61B 17/00* (2006.01)
*A61B 18/14* (2006.01)
(Continued)

(52) U.S. Cl.
CPC .............. *A61B 17/00* (2013.01); *A61B 17/32* (2013.01); *A61B 17/320068* (2013.01);
(Continued)

(58) Field of Classification Search
CPC . A61B 17/00; A61B 17/32; A61B 17/320068; A61B 18/1206;
(Continued)

(56) References Cited

U.S. PATENT DOCUMENTS 4,492,832 A 1/1985 Taylor
4,540,871 A 9/1985 Corrigall
(Continued)

FOREIGN PATENT DOCUMENTS

DE 2460481 6/1976
EP 1199040 4/2002
(Continued)

OTHER PUBLICATIONS

Search Report issued in corresponding EP Application No. 12191146.5-1652, Date of Search: Feb. 19, 2013.
(Continued)

*Primary Examiner* — Amanda Patton
(74) *Attorney, Agent, or Firm* — Nixon & Vanderhye P.C.

(57) ABSTRACT

A surgical instrument comprises a housing, an end effector carried by the housing, and one or more connections adapted to connect the surgical instrument to a controller such as an electrosurgical generator. The housing includes a plurality of handswitches located at different rotational positions around the housing. The handswitches comprise two handswitch sets the handswitches of each set being connected in to common so as to send the same signal to the controller whichever one of the handswitches is activated. In this way a user of the surgical instrument can send signals to the controller using any of the handswitches within a particular set, depending on the orientation of the surgical instrument.

13 Claims, 3 Drawing Sheets

Figure 1:
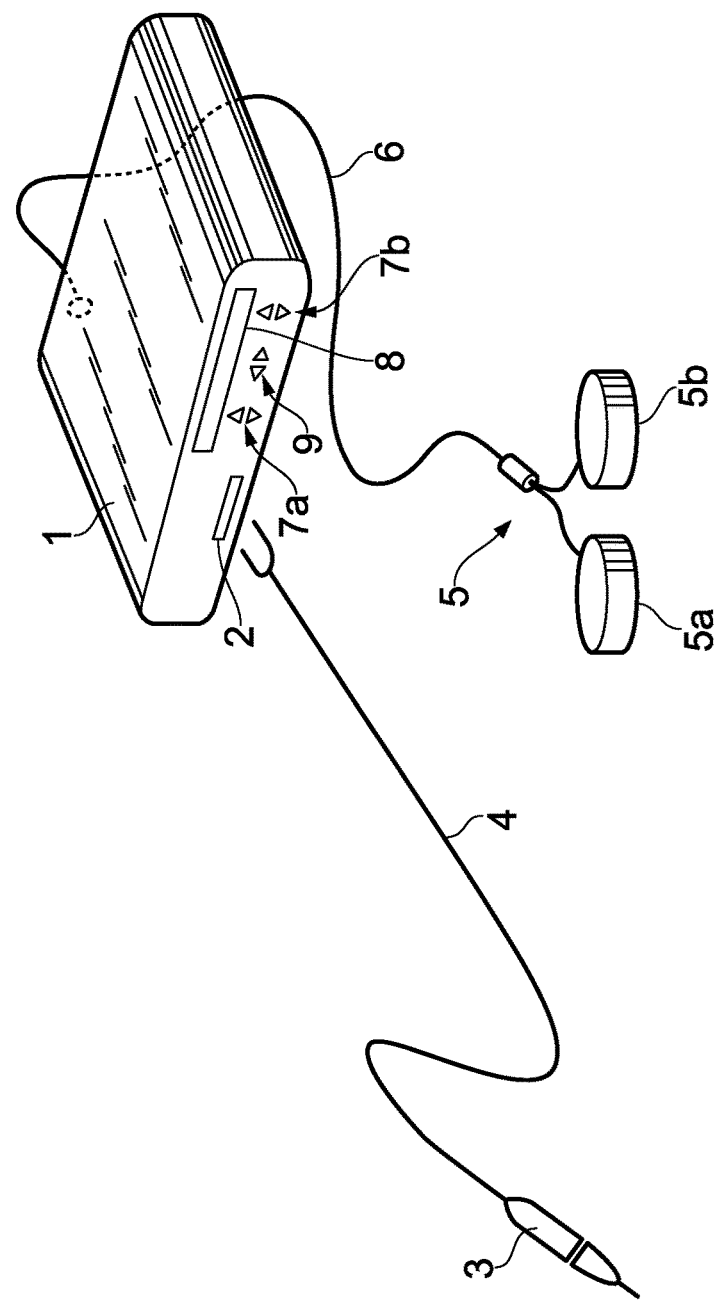

(51) Int. Cl.
  *A61B 17/32* (2006.01)
  *A61B 18/18* (2006.01)
  *A61B 18/12* (2006.01)
  *A61B 18/00* (2006.01)

(52) U.S. Cl.
  CPC .......... *A61B 18/1477* (2013.01); *A61B 18/18* (2013.01); *A61B 18/1206* (2013.01); *A61B 2017/00371* (2013.01); *A61B 2018/00916* (2013.01)

(58) Field of Classification Search
  CPC ................ A61B 18/1477; A61B 18/18; A61B 2017/00371; A61B 2018/00916
  See application file for complete search history.

(56) References Cited

U.S. PATENT DOCUMENTS

| | | | |
|---|---|---|---|
| 5,976,075 A | 11/1999 | Beane et al. | |
| 6,083,191 A | 7/2000 | Rose | |
| 6,896,674 B1 * | 5/2005 | Woloszko | A61B 18/1206 604/114 |
| 7,156,842 B2 * | 1/2007 | Sartor | A61B 18/1402 606/37 |
| 7,947,039 B2 | 5/2011 | Sartor | |
| 8,525,059 B2 * | 9/2013 | Berger | A61C 1/0007 200/512 |
| 2005/0113824 A1 | 5/2005 | Sartor et al. | |

FOREIGN PATENT DOCUMENTS

| | | |
|---|---|---|
| EP | 1872753 | 1/2008 |
| JP | 1992341254 | 11/1992 |
| JP | 2002177295 | 6/2002 |
| JP | 2004216170 | 8/2004 |
| JP | 2006102513 | 4/2006 |
| JP | 2008012315 | 1/2008 |
| JP | 2013516286 | 5/2013 |
| NL | 1017424 | 8/2002 |
| WO | WO 2011/085111 | 7/2011 |

OTHER PUBLICATIONS

Australian Patent Examination Report No. 1 in corresponding AU Application No. 2012251938, dated May 17, 2016.
UK Search Report for Application No. GB1119769.6, dated Mar. 6, 2012.
Office Action dated Oct. 11, 2016 in corresponding Japanese Patent Application No. 2012-248492.
English Translation of Office Action dated Oct. 11, 2016 in corresponding Japanese Patent Application No. 2012-248492.

* cited by examiner

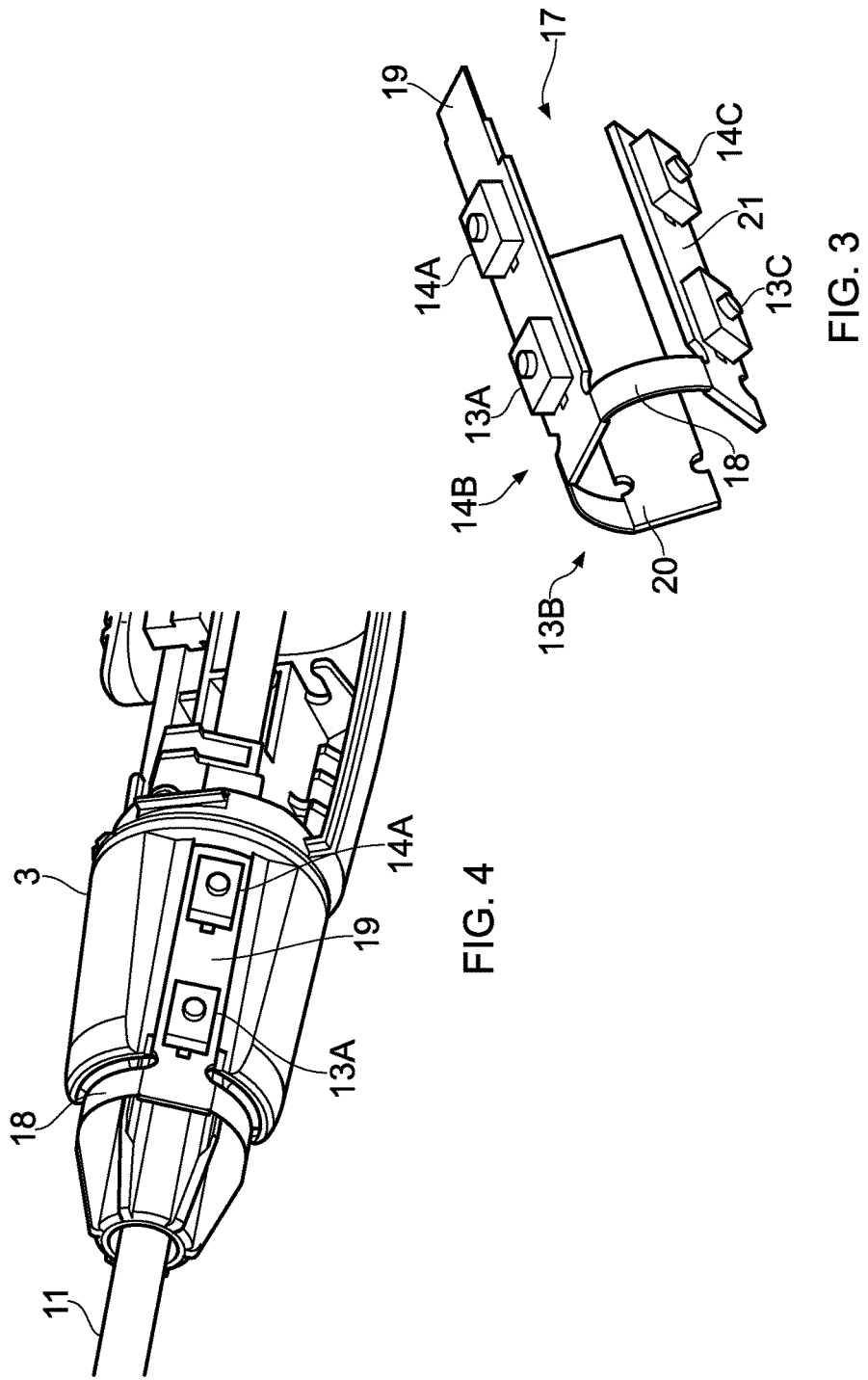

SURGICAL INSTRUMENT AND SYSTEM

This application claims priority to patent application GB1119769.6, filed 16 Nov. 2011, the entire contents of which are hereby incorporated herein by reference.

This invention relates to a surgical instrument for the treatment of tissue, and to a system including the surgical instrument along with a controller such as an electrosurgical generator. Such instruments are commonly used for the cutting/vaporisation and/or desiccation/coagulation of tissue in surgical intervention, to most commonly in "keyhole" or minimally invasive surgery. The terms "cutting" and "vaporization" relate to the removal of tissue, whether by resection or by the volumetric removal of tissue. Similarly, the terms "desiccation" and "coagulation" relate to the creation of lesions in tissue, the necrosis of tissue, and to the prevention of bleeding.

Surgical instruments requiring a controller have traditionally been activated by means of a footswitch located under the operating table, although more recently it has become known to activate the controller by means of one or more handswitches present on the instrument itself. U.S. Pat. No. 7,947,039 discloses one example of an instrument with multiple handswitches. The present invention attempts to provide an improvement to this type of surgical instrument.

Accordingly, a surgical instrument is provided, the surgical instrument including a housing, an end effector carried by the housing, and one or more connections adapted to connect the surgical instrument to a controller and communicate therewith, the housing further including a plurality of handswitches, two or more of the handswitches being located at different rotational positions around the housing, the two or more handswitches being connected in common so as to send the same signal to the controller whichever one of the two or more handswitches is activated, such that a user of the surgical instrument can send signals to the controller using any of the two or more handswitches depending on the orientation of the surgical instrument.

The provision of a plurality of handswitches disposed at different positions around the housing allows the user to activate the controller easily, regardless of the rotational orientation of the housing. This is an improvement on designs such as those of U.S. Pat. No. 7,947,039 in which the handswitches are really only usable in one orientation of the surgical instrument.

Where designers have previously attempted to solve the problem of handswitch activation in different orientations, they have tended to try to provide annular handswitches, as in U.S. Pat. No. 4,492,832. While this does allow for activation in any orientation, this type of handswitch is necessarily complicated in design and therefore relatively expensive and difficult to assemble. The annular handswitch of U.S. Pat. No. 4,492,832 also suffers from the problem of inadvertent activation, while manipulating the instrument. While relatively simple, the solution of the present invention does to provide easy activation in a number of orientations, while maintaining ease of manufacture and discouraging inadvertent activation.

The present invention is applicable to a number of different types of surgical instrument requiring a controller. The first type is an electrosurgical instrument, in which case the controller is an electrosurgical generator. Alternatively, the invention is applicable to a microdebrider or shaver instrument, in which case the controller is a motor adapted to rotate the blade of the instrument. Conceivably, the surgical instrument is an ultrasonic instrument, in which case the controller is a motor adapted to vibrate the blade or tip of the instrument. Whichever type of instrument is employed, the user needs to give instructions to the controller during use of the instrument, and this can be done using the handswitches located at different rotational positions with respect to the housing of the instrument.

According to a preferred arrangement, the plurality of handswitches includes three or more handswitches connected in common and located at different rotational positions around the housing. In this way, the user is able to activate a handswitch regardless of the orientation of the instrument. If the handswitches are disposed equidistantly around the housing, there is a handswitch every 120° around the circumference of the housing, such that the user is always be able to reach at least one handswitch, regardless of the orientation of the instrument.

The plurality of handswitches conveniently includes at least first and second sets of handswitches, each including two or more handswitches connected in common and located at different rotational positions around the housing, each of the first set of handswitches being adapted to send a first signal to the controller, and each of the second set of handswitches being adapted to send a second signal to the controller. Surgical instruments are becoming increasingly sophisticated, such that there is often more than a simple "on/off" control. By providing at least first and second sets of handswitches, different instructions can be given such as to increase or decrease power or velocity, or in the instance of an electrosurgical instrument, to change from a cutting to a coagulating RF waveform. In a preferred arrangement, the first and second sets of handswitches each include three or more handswitches connected in common and located at different rotational positions around the housing. Thus, there are at least six handswitches mounted on the instrument, three in one set and three in the other.

The plurality of handswitches are conveniently mounted on a single circuit board. According to a typical arrangement, the circuit board conveniently includes an annular section, adapted to extend wholly or partly around the surgical instrument. The circuit board also conveniently includes two or more cantilever sections extending from the annular section, each cantilever section containing at least one handswitch. In this way, each cantilever section contains the handswitches for a particular angular orientation, whether in a single set or two or more different sets. The handswitches can therefore be provided on a single circuit board, making for a low cost manufacture and a simple assembly of the surgical instrument.

As stated previously, the surgical instrument is conceivably an electrosurgical instrument, in which case the end effector is at least one electrode, and the one or more connections are adapted to connect the electrosurgical instrument to an electrosurgical generator for supplying energy to the at least one electrode. Alternatively, the surgical instrument is conceivably a mechanical microdebrider, in which case the end effector is a rotatable blade, and the one or more connections are adapted to connect the surgical instrument to a motor for rotating the blade. Finally, the surgical instrument is conceivably an ultrasonic instrument, in which case the end effector is an oscillating tip, and the one or more connections are adapted to connect the surgical instrument to a generator for oscillating the tip.

Conveniently, at least one of the handswitches is provided with a tactile identification adapted to distinguish it from other handswitches provided on the surgical instrument. A raised pimple or other identifier present on one of the handswitches allows a user of the instrument to establish the orientation of the surgical instrument purely from touch rather than from sight. As the instrument contains multiple handswitches, the handswitches themselves can no longer be used to orient the instrument, as would be the case with a single handswitch. The provision of a tactile indicator reinstates the handswitch as a means of orientation. While it is normally only necessary to provide an indication on one handswitch, conceivably each handswitch could include its own unique tactile identification, such as one pimple, two pimples and three pimples respectively for a three-handswitch instrument.

The surgical instrument conveniently also includes a holding area provided opposite each of the handswitches, the holding area being free from other handswitches and adapted to receive the thumb or finger of a user. In this way, the user can operate each handswitch with a first finger, and with another finger or thumb placed opposite the handswitch in order to provide the appropriate pressure. If a holding area is to be provided in this way, then three handswitches has proved to be the preferred number, as this automatically provides a holding area if the handswitches are disposed equidistantly around the housing of the surgical instrument.

According to a preferred arrangement, the invention relates to an electrosurgical system including
  i) an electrosurgical generator,
  ii) an electrosurgical instrument including a housing, one or more electrodes carried by the housing, and one or more connections for connecting the electrosurgical instrument to the generator, the electrosurgical instrument further including a plurality of handswitches, two or more of the handswitches being located at different rotational positions around the instrument, the two or more handswitches being connected in common so as to send the same signal to the electrosurgical generator whichever one of the two or more handswitches is activated, such that a user of the electrosurgical instrument can send signals to the generator using any of the two or more handswitches depending on the orientation of the electrosurgical instrument.

The generator preferably includes a source of radio frequency energy capable of supplying either a coagulating RF waveform or a cutting RF waveform, and the plurality of handswitches on the electrosurgical instrument includes at least first and second sets of handswitches, each including two or more handswitches connected in common and located at different rotational positions around the electrosurgical instrument. In this way, the first set of handswitches is adapted to cause the generator to supply the cutting RF waveform, and the second set of handswitches is adapted to cause the generator to supply the coagulating RF waveform. Regardless of the orientation of the electrosurgical instrument, the user is able to activate one of the handswitches, either to initiate the cutting RF waveform or the coagulating RF waveform, as desired.

Figure 2:
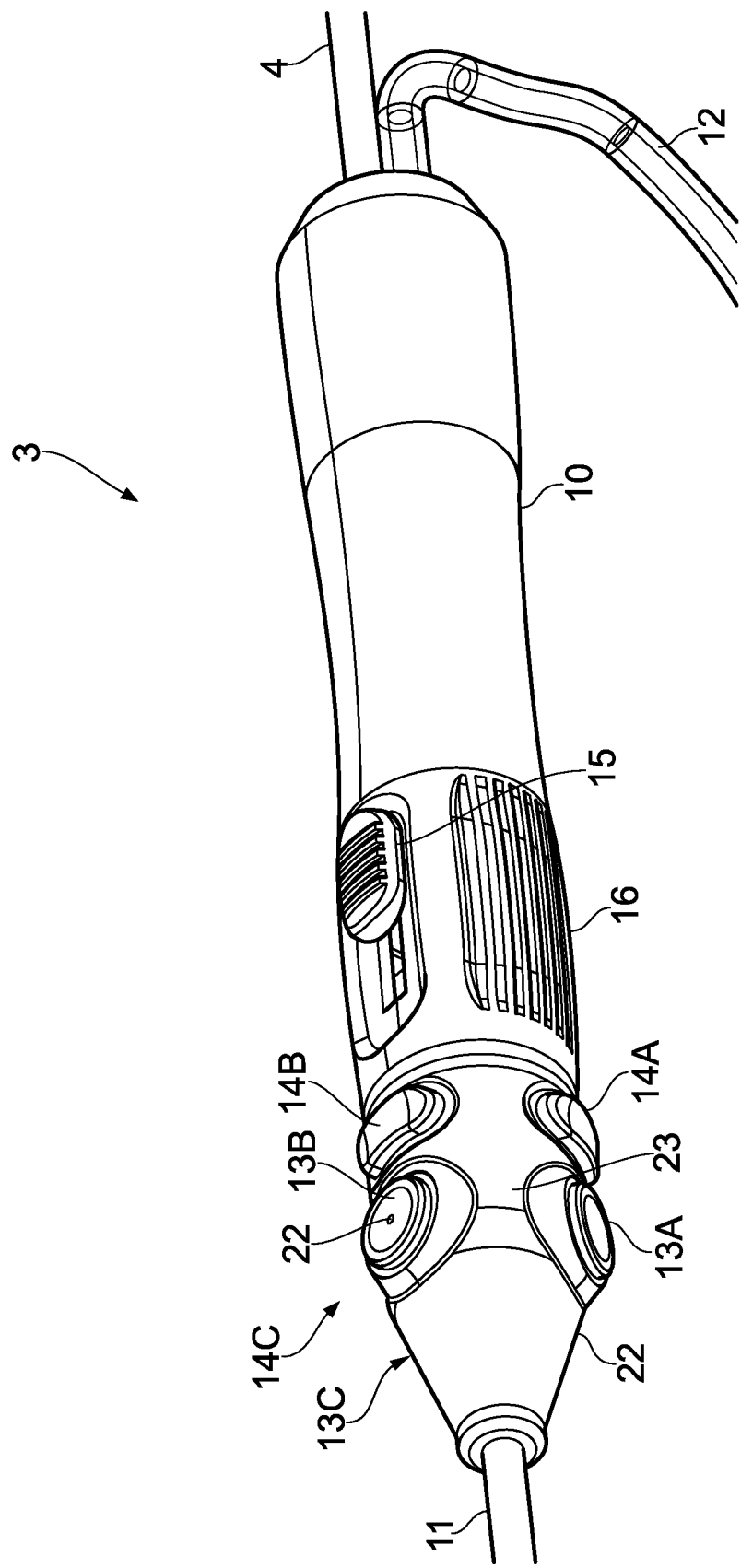

The invention will now be further described, by way of example only, with reference to the accompanying drawings, in which:

FIG. 1 is a schematic diagram of an electrosurgical system including an electrosurgical instrument in accordance with the present invention, FIG. 2 is a perspective view of an electrosurgical instrument in accordance with the present invention, FIG. 3 is a perspective view of a circuit board forming part of the electrosurgical instrument of FIG. 2, and FIG. 4 is a perspective view of the electrosurgical instrument of FIG. 2, shown in a partly assembled condition.

Referring to the drawings, FIG. 1 shows a conventional electrosurgical apparatus including a generator 1 having an output socket 2 providing a radio frequency (RF) output, for an instrument 3 via a connection cord 4. Activation of the generator 1 may be performed by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

FIG. 2 shows the instrument 3 in more detail. The instrument 3 comprises a cylindrical housing 10 having an elongate shaft 11 emerging from its distal end. The shaft is provided at its distal end with an electrosurgical assembly (not shown). The shaft is provided with a suction lumen (not shown) connected through the housing 10 to a suction tube 12 located alongside the electrical connection cord 4 at the proximal end of the housing.

The housing 10 is provided with a plurality of handswitch buttons as will be further described. A first set of three handswitch buttons 13A, 13B, 13C are provided on the housing 10 so as to be equidistantly spaced one from another at 120° intervals around the housing. Handswitch button 13C is located on the far side of the housing and cannot be seen in FIG. 2. Handswitch 13B is provided with a tactile indicator such as a pimple 22 in order to provide a non-visual orientation signal to the user of the instrument. A plain area 23 is provided in between each of the handswitches 13A, 13B, 13C, the holding area being designed so that the user can place a finger or thumb in a holding area 23 while operating the handswitch located directly opposite.

A second set of three handswitch buttons 14A, 14B, 14C are provided on the housing 10 proximal of the handswitch buttons 13A, 13B, 13C. As before, the handswitch buttons 14A, 14B, 14C are equidistantly spaced one from another at 120° intervals around the housing. Handswitch button 14C is located on the far side of the housing and cannot be seen in FIG. 2. The handswitch buttons 13A, 13B, 13C of the first set are designated "cutting" buttons and are generally circular in shape. In contrast, the handswitch buttons 14A, 14B, 14C of the second set are designated "coagulation" buttons and are elongate in shape. The housing 10 is also provided with a slider button 15 for controlling the amount of suction delivered to the shaft 11, and with a ridged area 16 for assisting with the gripping of the housing by a user of the instrument 3.

FIG. 3 shows a circuit board 17 comprising an annular section 18 and three cantilevered sections 19, 20, 21 depending therefrom. Handswitch buttons 13A, 14A are located on cantilever section 19, handswitch buttons 13B, 14B on cantilever section 20, and handswitch buttons 13C, 14C on cantilever section 21. FIG. 4 shows the circuit board 17 located on the instrument 3 before a cover plate 22 is attached, as shown in FIG. 2. Handswitch buttons 13A, 13B, 13C of the first set are connected in common such that a cutting activation signal is sent to the generator 1 regardless of which handswitch 13A, 13B, 13C is pressed. Similarly, handswitch buttons 14A, 14B, 14C of the second set are also connected in common, such that a coagulation activation signal is sent to the generator 1 regardless of which handswitch 14A, 14B, 14C is pressed.

The operation of the instrument 3 will now be described. The user of the instrument 3 grasps the housing 10 and manipulates the instrument into position adjacent the tissue to be treated. This may mean rotating the instrument such that it is not in the orientation shown in FIG. 2. When the user wishes to cause the generator 1 to provide a cutting RF waveform to the electrode assembly at the tip of the shaft 11, the user presses any one of the handswitch buttons 13A, 13B, 13C of the first set, the choice of button depending on whichever button is easiest to press given the orientation of the housing 10. Similarly, when the user wishes to cause the generator 1 to provide a coagulating RF waveform to the electrode assembly at the tip of the shaft 11, the user presses any one of the handswitch buttons 14A, 14B, 14C of the second set, the choice of button once again depending on whichever button is easiest to press given the orientation of the housing 10. The provision of multiple buttons avoids the user having to re-orient the housing in order to activate a single button, or the user having to stretch in order to reach a button located on the opposite side of the housing. Whatever the orientation of the housing, the user is always easily able to reach one of the buttons, as they are provided around the circumference of the housing 10.

Other variations can be envisaged without departing from the scope of the present invention. Four or more buttons can be provided around the circumference of the housing 10, as opposed to the three buttons illustrated in FIGS. 2 to 4. A third set of buttons can be provided, either instead of the slider button 15 or in addition thereto. For example, the third set of buttons can be used to change the power levels of the cutting and coagulating RF waveforms, or change the "mode" of operation of the generator, for example to provide a "blended" cutting and coagulating RF waveform. Whatever the function of the handswitch buttons provided, the provision of multiple buttons connected in common and located in different positions around the housing 10 allows for ease of operation whatever the orientation of the instrument.

What is claimed is:

1. A surgical instrument including
   a housing,
   an end effector carried by the housing,
   at least one or more connections adapted to connect the surgical instrument to a controller and communicate therewith, and
   at least three separate handswitches located at different rotational positions around the housing so as to be spaced from one another to thereby provide at least one of the at least three handswitches adjacent to fingers and/or a thumb of a user of the surgical instrument, regardless of rotational orientation of the housing, the at least three handswitches each being activatable independently of the others of the at least three handswitches, yet connected in common to the controller so as to send the same signal to the controller, whichever one of the at least three handswitches is activated, such that the user of the surgical instrument can send signals to the controller using any of the three or more handswitches depending on the orientation of the surgical instrument,
   wherein the at least three handswitches include at least first and second sets of handswitches, each set of handswitches including at least three handswitches connected in common and located at different rotational positions around the housing, each of the first set of handswitches being adapted to send a first signal to the controller, and each of the second set of handswitches being adapted to send a second signal to the controller, and the plurality of handswitches are mounted on a single circuit board, the circuit board including an annular section, adapted to extend at least partly around the surgical instrument, and at least three cantilever sections extending from the annular section, each cantilever section containing at least one handswitch from the first set of handswitches and one handswitch from the second set of handswitches.

2. The surgical instrument according to claim 1, wherein the surgical instrument is an electrosurgical instrument, the end effector is at least one electrode, and the at least one connection is adapted to connect the electrosurgical instrument to an electrosurgical generator for supplying energy to the at least one electrode.

3. The surgical instrument according to claim 1, wherein the surgical instrument is a mechanical microdebrider, the end effector is a rotatable blade, and the at least one connection is adapted to connect the surgical instrument to a motor for rotating the blade.

4. The surgical instrument according to claim 1, wherein the surgical instrument is an ultrasonic instrument, the end effector is an oscillating tip, and the at least one connection is adapted to connect the surgical instrument to a motor for oscillating the tip.

5. The surgical instrument according to claim 1, wherein at least one of the handswitches is provided with a tactile identification adapted to distinguish it from other handswitches provided on the surgical instrument.

6. The surgical instrument according to claim 1, wherein a holding area is provided opposite each of the handswitches, the holding area being free from other handswitches and adapted to receive the thumb or finger of a user.

7. An electrosurgical system including
   i) an electrosurgical generator,
   ii) an electrosurgical instrument including
      a housing,
      at least one electrode carried by the housing,
      at least one connection for connecting the electrosurgical instrument to the generator, and
      at least three separate handswitches located at different rotational positions around the instrument so as to be spaced from one another to thereby provide at least one of the at least three handswitches adjacent to fingers and/or a thumb of a user of the surgical instrument, regardless of rotational orientation of the instrument, the at least three handswitches each being activatable independently of the others of the at least three handswitches, yet connected in common to the controller so as to send the same signal to the electrosurgical generator whichever one of the at least three handswitches is activated, such that a user of the electrosurgical instrument can send signals to the generator using any of the at least three handswitches depending on the orientation of the electrosurgical instrument,
   wherein the at least three handswitches include at least first and second sets of handswitches, each set of handswitches including at least three handswitches connected in common and located at different rotational positions around the housing, each of the first set of handswitches being adapted to send a first signal to the controller, and each of the second set of handswitches being adapted to send a second signal to the controller, and the plurality of handswitches are mounted on a single circuit board, the circuit board including an annular section, adapted to extend at least partly around the surgical instrument, and at least three cantilever sections extending from the annular section, each cantilever section containing at least one handswitch from the first set of handswitches and one handswitch from the second set of handswitches.

8. The electrosurgical system according to claim 7, wherein the generator includes a source of radio frequency energy capable of supplying a coagulating RF waveform and a cutting RF waveform.

9. The electrosurgical system according to claim 8, wherein the generator includes a source of radio frequency energy capable of supplying a coagulating RF waveform and a cutting RF waveform, and wherein the first set of handswitches is adapted to cause the generator to supply the cutting RF waveform, and the second set of handswitches is adapted to cause the generator to supply the coagulating RF waveform.

10. A surgical instrument including:
a housing,
an end effector carried by the housing,
at least one or more connections that connect the surgical instrument to a controller and that allow the surgical instrument to communicate with the controller, and
at least three separate handswitches equidistantly spaced one from another around the housing so as to thereby provide at least one of the at least three handswitches adjacent to a user's fingers and/or thumb regardless of rotational orientation of the housing,
the at least three handswitches each being activatable independently of the others of the at least three handswitches, yet connected in common to the controller so as to send the same signal to the controller, whichever one of the at least three handswitches is activated, such that the user of the surgical instrument can send signals to the controller using any of the three or more handswitches, depending on the orientation of the surgical instrument,
wherein the at least three handswitches include at least first and second sets of handswitches, each set of handswitches including at least three handswitches connected in common and located at different rotational positions around the housing, each of the first set of handswitches being adapted to send a first signal to the controller, and each of the second set of handswitches being adapted to send a second signal to the controller,
and the plurality of handswitches are mounted on a single circuit board, the circuit board including an annular section, adapted to extend at least partly around the surgical instrument, and at least three cantilever sections extending from the annular section, each cantilever section containing at least one handswitch from the first set of handswitches and one handswitch from the second set of handswitches.

11. The surgical instrument according to claim 10, wherein the at least three separate handswitches are three separate handswitches equidistantly spaced one from another at 120° intervals around the housing.

12. The surgical instrument according to claim 10, wherein the at least first and second sets of handswitches are located at different longitudinal positions along the housing.

13. The surgical instrument according to claim 12, wherein the first signal sent to the controller causes the controller to change to a cutting RF waveform, and wherein the second signal sent to the controller causes the controller to change to a coagulating RF waveform.

* * * * *